United States Patent [19]

Shibata et al.

[11] Patent Number: 4,936,975
[45] Date of Patent: Jun. 26, 1990

[54] CHLORIDE ION-SELECTIVE ELECTRODE

[75] Inventors: Yasuhisa Shibata, Ibaraki; Satoshi Ozawa; Naoto Oki, both of Hitachi; Hiroyuki Miyagi, Mito, all of Japan

[73] Assignee: Hitachi, Ltd., Tokyo, Japan

[21] Appl. No.: 221,219

[22] Filed: Jul. 19, 1988

[30] Foreign Application Priority Data

Jul. 20, 1987 [JP] Japan .................. 62-178917

[51] Int. Cl.$^5$ ............................ G01N 27/30
[52] U.S. Cl. .................... 204/418; 204/416; 204/153.13
[58] Field of Search ............ 204/418, 1 T, 416

[56] References Cited

U.S. PATENT DOCUMENTS 4,519,891 5/1985 Sugahara et al. ............. 204/418

OTHER PUBLICATIONS

Mikrochimia Acta, 1984, pp. 1-16.

Primary Examiner—John F. Niebling
Assistant Examiner—David G. Ryser
Attorney, Agent, or Firm—Fay, Sharped, Beall, Fagan, Minnich & McKee

[57] ABSTRACT

A liquid film type, chloride ion-selective electrode is provided with the present invention, which comprises a sensitive film containing a polymeric material as a support film material, a tetraalkyl ammonium salt with four alkyl group each having 10-24 carbon atoms as a chloride ion-sensitive substance, and a mixture of a linear alcohol having a low dielectric constant with at leastg 10 carbon atoms and an organic compound having a dielectric constant higher than that of said linear alcohol as plasticizer. This electrode has a high selectivity over lipophilic anions and hydrophilic anions, high accuracy ion measurements, and a long life.

13 Claims, 3 Drawing Sheets

N = 24
R = .995
Y = -3.132 + 1.031 X
X(Ave) = 102.833 +-(10.957)
Y(Ave) = 102.917 +-(11.359)
SYX = 1.19

N = 22
X(Ave) = 104.7 +−(9.3)
Y(Ave) = 100.3 +−(9.3)
R = 0.9808
Y = 0.98X+(−2.61)
SYX = 1.91

CHLORIDE ION-SELECTIVE ELECTRODE

BACKGROUND OF THE INVENTION a. FIELD OF THE INVENTION

The present invention relates to a chloride ion-selective electrode, and particularly to a liquid film type, chloride ion-selective electrode based on a polymer support film suitable for measuring a chloride ion in body liquids.

b. RELATED ART STATEMENT

It is known to use, a chloride ion-selective electrode for measuring a chloride ion in body liquids, having a solid film type electrode comprising silver chloride and silver sulfide or a liquid film type electrode comprising a sensitive film which contains an ion exchange substance as a sensitive substance in a synthesized polymer support of polyvinyl chloride, etc. The former solid film type electrode is undesirably susceptible to influences by other halogen ions such as bromide ions and also by sulfide ions.

Japanese Patent Kokai (Laid-open) No. 57-77952 (1982) discloses a liquid film type electrode comprising a sensitive film containing a polymer resin as a support film material, methyltridecylammonium chloride as a sensitive substance, and n-tetradecyl alcohol as a plasticizer. U.S. Pat. No. 4,519,891 discloses a liquid film type electrode comprising a sensitive film containing a polyvinyl chloride as a support film material, dimethyldioctadecylammonium chloride as a sensitive substance, and a combination of n-tetradecyl alcohol and o-nitrophenyloctylether as a plasticizer. Microcimica Acta, [Wein], 1984, III, 1–16, describes a liquid film type electrode comprising a sensitive film containing a vinyl chloride polymer resin as a support film material, tetradodecylammonium chloride as a sensitive substance, and dioctyl sebacate as a plasticizer.

These known liquid film type electrodes have large error of measurement due to influences by substances such as lipophilic ions which are apt to be deposited on the surface of the sensitive film, and that the effective life of the electrode is rather short due to a leaching or dissolution of the sensitive substance i.e. ion exchange substance from the sensitive film into the liquid phase and also due to a deposition or adsorption of proteins and the like onto the surface of the sensitive film.

Furthermore, in the case of the known liquid type electrodes supported on a polymer resin, the selectivity over hydrophilic anions such as bicarbonate ions is decreased with a decrease of the selectivity over lipophilic anions, and the selectivity over the lipophilic anions is considerably decreased by enhancing the selectivity over hydrophilic anions such as bicarbonate ions. It is therefore important to enhance the selectivity over both hydrophilic anions and lipophilic anions, in order to decrease measurement errors and to improve measurement accuracy.

When the known liquid film type, chloride ion-selective electrodes supported on a polymeric material are employed for measuring chloride ions in blood, it is observed that the selectivity over lipophilic anions and hydrophilic anions is not satisfactorily high, so that these electrodes lack sufficient accuracy. Furthermore, the known liquid film type, chloride ion-selective electrodes based on a polymer support film do not prevent a leaching or dissolution of the sensitive substance from the support film, so that the electrodes have a relatively short effective life.

SUMMARY OF THE INVENTION

An object of the present invention is to provide a liquid film type, chloride ion-selective electrode with a good selectivity over lipophilic anions and hydrophilic anions, which can produce correct results of measurements and has a long life.

To attain the above-mentioned object, the present invention provides a liquid film type, chloride ion-selective electrode comprising a sensitive film containing a polymeric material as a support film material and a quaternary ammonium salt as a chloride ion-sensitive substance, characterized in that the sensitive film contains a tetraalkylammonium salt with four alkyl groups each having 10–24 carbon atoms as the chloride ion-sensitive substance, and a mixture of a linear alcohol having at least 10 carbon atoms with a low dielectric constant and an organic compound with a dielectric constant higher than that of said linear alcohol as a plasticizer.

DETAILED DESCRIPTION OF THE INVENTION

Figure 1:
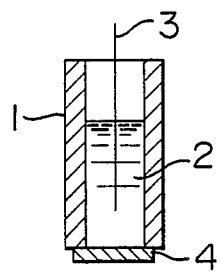
FIG. 1 is a schematic view showing the structure of a chloride ion-selective electrode according to an embodiment of the present invention.

A liquid film type, chloride ion-selective electrode comprises a sensitive film containing a polymeric material such as polyvinyl chloride, a plasticizer and a sensitive substance. First of all, an explanation will be made about the use of quaternary ammonium chlorides as the sensitive substance.

Quaternary ammonium chlorides can be classified in the following four types.

Type (1)

Type (2)

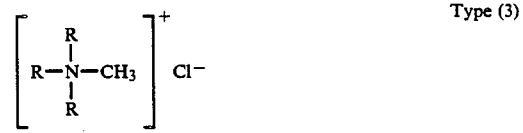

Type (3)

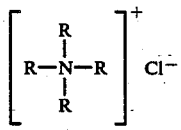

Type (4)

In the above formulae, R represents an aliphatic alkyl group having at least 8 carbon atoms.

The lipophilicity of compounds of type (1) is lower than that of types (2), (3) and (4), so that it is not preferred to use compounds of type (1) as the sensitive substance in a chloride ion-selective electrode, from the viewpoint of stability and effective life of the electrode.

On the other hand, the lipophilicity of compounds of type (2), (3) and (4) can be readily intensified with increasing number of R groups, so that these compounds have a practical utility as the sensitive substance in a chloride ion-selective electrode. In practice, compounds of type (2) and (3) are used at present.

In an ammonium compound of type (4), the four long alkyl groups having a bulky volume are present around the nitrogen atom, so that it is considered in view of molecular structure that, as compared with the nitrogen atom in an ammonium compound of type (1), (2) or (3), the nitrogen atom in an ammonium compound of type (4) is more difficultly attacked by anions other than the chloride ion ($Cl^-$) bonded to the ammonium group contained in said compound of type (4). Therefore, it is expected that a chloride ion-selective electrode containing a compound of type (4) as a sensitive substance has a better selectivity over various anions, as compared with a somewhat similar chloride ion-selective electrode containing a compound of type (1), (2) or (3) as a sensitive substance. However, when a tetraalkylammonium salt of type (4) is used as the sensitive substance in a chloride ion-selective electrode, the choice of a plasticizer capable of dissolving said ammonium salt and establishing a dissociated ionized state of cations and anions is largely limited. If an appropriate plasticizer is not used, the basic properties of the resultant electrodes such as responsiveness, sensitivity and the like will be unsatisfactory. As the number of the carbon atoms contained in the alkyl group increases, the choice of a suitable plasticizer is more limited. For the reasons mentioned above, no one has found, up to date, a compound which belongs to type (4) and which has fundamental properties including selectivity sufficient for an analysis of chloride ions in body liquids. A practically useful, chloride ion-selective electrode containing a compound of type (4) has not been produced yet. Therefore, when a compound of type (4) is employed as a sensitive substance, it is important to select an optimum combination of such a sensitive substance and a plasticizer. The total number of carbon atoms contained in a compound of type (4) is larger than that contained in a compound of type (2) or (3), with the proviso that the long alkyl groups contained in the former compound are the same as those contained in the latter compound. Such being the case, compounds of type (4) have a higher lipophilicity as compared with that of compounds of types (2) and (3), and therefore have an advantage that the leaching or dissolution of compounds of type (4) as the sensitive substance from the sensitive film is very small, so that the resulting electrodes have a long life.

Hereinafter, a detailed explanation will be made about preferred embodiments according to the present invention.

FIG. 1 is a schematic cross-sectional view showing the structure of a chloride ion-selective electrode according to an embodiment of the present invention, where an internal electrolyte 2 containing 10 mmol/liter of NaCl is stored in a cylindrical body 1, and an internal electrode (Ag/AgCl) 3 is dipped in the internal electrolyte 2, while a sensitive film 4 is formed at one end of the body 1. The sensitive film 4 contains a polymeric material such as polyvinyl chloride, wherein a chloride ion-sensitive substance and a plasticizer are dispersed at their optimal concentrations.

According to the present invention, tetraalkylammonium chlorides are used as the ion exchange substances of quaternary ammonium salt type, which serve as a chloride ion-sensitive substance. Preferred examples of said quaternary ammonium salts are tetraalkylammonium chlorides with four alkyl groups each having 10-24 carbon atoms, including tetradodecylammonium chloride, tetratetradecylammonium chloride, tetracetylammonium chloride, tetraoctadecylammonium chloride, etc. Tetracetylammonium chloride and tetraoctadecylammonium chloride are particularly preferred. When these quaternary ammonium salts are used as the sensitive substances, a considerable improvement can be made on the selectivity of the electrode over lipophilic anions and hydrophilic anions, on the accuracy of measurement and on the electrode life. Furthermore, such a sensitive film can be produced very easily. The electrodes are less susceptible to noises resulting from too high a resistance. As mentioned above, the use of the tetraalkylammonium chlorides according to the present invention can have a number of advantages.

According to a first preferred embodiment of the present invention, tetracetylammonium chloride is used as a chloride ion-sensitive substance. The ion-sensitive film 4 is prepared in the following manner. There are mixed 15% by weight of tetracetylammonium chloride as a chloride ion-sensitive substance, 30% by weight of n-tetradecyl alcohol having a dielectric constant of about 4.5 as a plasticizer of low dielectric constant, 10% by weight of o-nitrophenyloctylether having a dielectric constant of about 24 as a plasticizer of high dielectric constant and 45% by weight of polyvinyl chloride as a film support material, and the resulting mixture is dissolved in tetrahydrofuran as a solvent. The resulting solution is poured into a mold of definite shape, and the solvent is removed by evaporation to obtain a sheet of sensitive film for chloride ions. The sheet is cut into a disc form corresponding to the size of body 1 of FIG. 1, and then bonded to the end of body 1.

In the first preferred embodiment mentioned above, n-tetradecyl alcohol is used as the plasticizer of low dielectric constant, but the plasticizers of low dielectric constant are not limited thereto. Linear alcohols with a good lipophilicity having at least 10 carbon atoms are suitable as plasticizers of low dielectric constant. Particularly, linear alcohols having 10-20 carbon atoms with a dielectric constant of not more than 10 have a good effect. An appropriate content of a linear alcohol having a low dielectric constant in the sensitive film is 10-40% by weight.

When only a linear alcohol having a low dielectric constant is used as a plasticizer in the sensitive film, the resulting liquid film type chloride ion-selective electrodes are unsatisfactory with respect to responsiveness and stability, because the dielectric constant of such a linear alcohol is too low to sufficiently cause a reaction condition for shifting the equilibrium in an ion dissociation reaction, represented by the following equation (1), toward the right side.

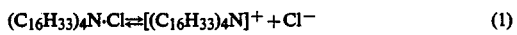

$$(C_{16}H_{33})_4N \cdot Cl \rightleftharpoons [(C_{16}H_{33})_4N]^+ + Cl^- \tag{1}$$

In the first preferred embodiment, another plasticizer should be also contained in the sensitive film, so that a mixture of two kinds of plasticizers is present in the sensitive film. Namely, an organic compound with a high lipophilicity having a dielectric constant of at least 15 is also contained as another plasticizer. When such another plasticizer is also used, it is possible to adequately shift the ion dissociation reaction of the formula (1) toward the right side, that is, in the direction to complete the dissociation, so that the resultant chloride ion-selective electrodes can work effectively.

As the plasticizers of high dielectric constant, it is possible to use, for instance, o-nitrophenyloctylether and related compounds thereof such as o-nitrophenylphenylether, 2-fluoro-2'-nitrodiphenylether and the like; nitrobenzene and derivatives thereof such as o-, m-, and p-nitrotoleuene; and acetophenone etc. An appropriate content of these organic compounds having a high dielectric constant in the sensitive film is 3–20% by weight.

In a second preferred embodiment, there are mixed 15% by weight of tetraoctadecylammonium chloride, 30% by weight of n-tetradecyl alcohol, 10% by weight of o-nitrophenyloctylether and 45% by weight of polyvinyl chloride, and the resulting mixture is dissolved in tetrahydrofuran. A sensitive film is prepared therefrom in the same manner as in the first preferred embodiment, and then fixed to the electrode body.

An appropriate content of tetraacetylammonium chloride or tetraoctadecylammonium chloride dispersed in the sensitive film is 3–30% by weight from the viewpoint of responsiveness, sensitivity, and membrane resistance to be decreased. If another tetraalkylammonium chloride mentioned above is used as the sensitive substance according to the present invention, an appropriate content thereof in the sensitive film is also 3–30% by weight for the reason mentioned above.

In a third preferred embodiment, two kinds of linear alcohols are used as the alcohol type plasticizer. There are mixed 15% by weight of tetraoctadecylammonium chloride as a sensitive substance, 25% by weight of n-tetradecyl alcohol as an alcohol component of a first class, 5% by weight of n-tridecyl alcohol is an alcohol component of a second class, 5% by weight of o-nitrophenyloctylether and 50% by weight of polyvinyl chloride, and a sensitive film is prepared from the resulting mixture in the same manner as in the first preferred embodiment, and then fixed to the electrode body 1. n-Tridecyl alcohol can increase the solubility of sensitive substances and reduce the crystallization of another plasticizer. An appropriate content of n-tridecyl alcohol is 1–15% by weight from the viewpoint of selectivity over various anions, electrode resistance, etc. In this embodiment, n-tridecyl alcohol is used as an alcohol component of a second class, but the alcohols of the second class are not limited thereto. Any linear alcohols having a similar effect may also be used.

In a fourth preferred embodiment 2-fluoro-2'-nitrodiphenylether with a dielectric constant of about 50, which has a structure closely related to that of o-nitrophenyloctylether, is used as an organic compound of high dielectric constant. A sensitive film is prepared which comprises 15% by weight of tetraoctadecylammonium chloride, 25% by weight of n-tetradecyl alcohol as a linear alcohol component of first class, 5% by weight of n-tridecyl alcohol as a linear alcohol component of second class, 5% by weight of 2-fluoro-2'-nitrodiphenylether and 50% by weight of polyvinyl chloride. The organic compound employed in this embodiment has a very high dielectric constant, and can promote the shifting of the equilibrium in the ion dissociation reaction of the formula (1) toward the right side, so that the electrode resistance can be decreased.

In the above-mentioned preferred embodiments, a polyvinyl chloride is used as a support film material for carrying the sensitive substances and plasticizers. It is also possible to use other polymeric materials such as polycarbonates, silicone rubbers, epoxy resins, etc. When the content of polymeric materials in a sensitive film is below 25% by weight, the mechanical strength of the sensitive film becomes very low owing to other components involved. On the other hand, when the content of polymeric materials is above 60% by weight, the electrode resistance becomes undesirably high, so that a stable electrode operation cannot be carried out. Therefore, an appropriate content of polymeric materials in a sensitive film is 25–60% by weight.

Effects of the foregoing preferred embodiments according to the present invention will be described below.

For comparison of the present invention, three examples of the prior art are given below. A first example of the prior art is a modification of an anion-selective electrode shown in Japanese Patent Kokai (Laid-open) No. 57-77952, where the sensitive film contains 15% by weight of methyltridodecylammonium chloride as a sensitive substance, 30% by weight of n-tetradecyl alcohol as a single plasticizer and 55% by weight of polyvinyl chloride as a polymeric material. A second example of the prior art is based on an anion-selective electrode disclosed in U.S. Pat. No. 4,519,891, where the sensitive film contains 15% by weight of dimethyldioctadecylammonium chloride as a sensitive substance, 30% by weight of n-tetradecyl alcohol and 10% by weight of o-nitrophenyloctylether as a plasticizer, and 45% by weight of polyvinyl chloride as a polymeric material. A third example of the prior art is based on an anion-selective electrode disclosed in Microchimica Acta, [Wein], 1984, III, 1–16, where the sensitive film contains 6% by weight of tetradodecylammonium chloride as a sensitive substance, 65% by weight of dioctyl sebacate as a plasticizer and 29% by weight of polyvinyl chloride as a polymeric material.

Figure 2:
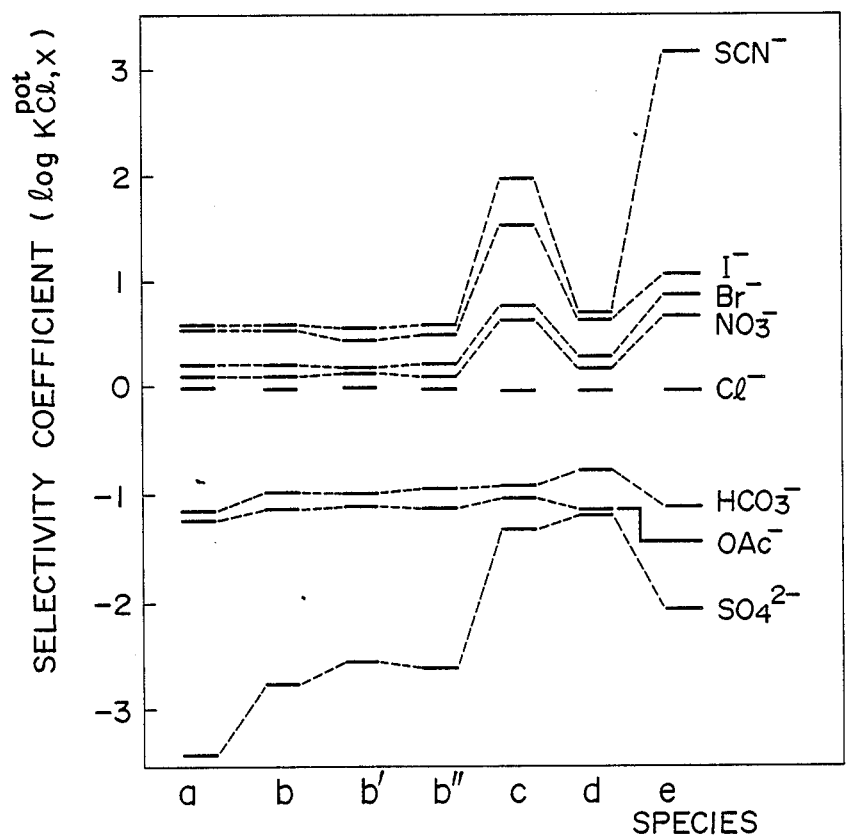
FIG. 2 is a diagram showing selectivity coefficients of a chloride ion-selective electrode according to the present invention and of a known chloride ion-selective electrode over various species of anions.

In FIG. 2 are shown results of measuring selectivity coefficients over various ion species, based on the chloride ion, by the electrodes of the first, second, third and fourth preferred embodiments according to the present invention and the electrodes of the first, second and third examples of prior art, where a, b, b' and b" show the results by the first, second, third and fourth preferred embodiments, respectively, according to the present invention, and c, d and e show the results by the first, second and third examples of prior art, respectively.

It is obvious from FIG. 2 that the electrodes of the present invention have a remarkable improvement in selectivity over hydrophilic anions such as sulfate ions ($SO_4^{2-}$), bicarbonate ions ($HCO_3^-$), etc., and over anions of high lipophilicity such as thiocyanate ions ($SCN^-$), etc., as compared with the prior art electrodes.

Figure 3:
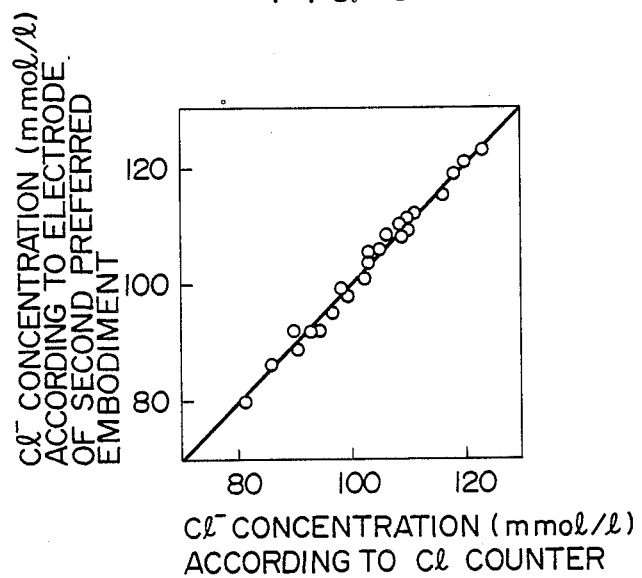
FIGS. 3 and 4 are diagrams showing correlations to coulometry when a commercially available, controlled serum is used, FIG. 3 showing a correlation to a preferred embodiment of the present invention and FIG. 4 showing a correlation to a conventional example.

FIG. 3 shows a correlation between measurements of chloride ion concentration of 24 species of commercially available, controlled serum by the electrode of the second preferred embodiment according to the present invention and those by the standard method. The standard method is a coulometry method (Cl counter).

Figure 4:
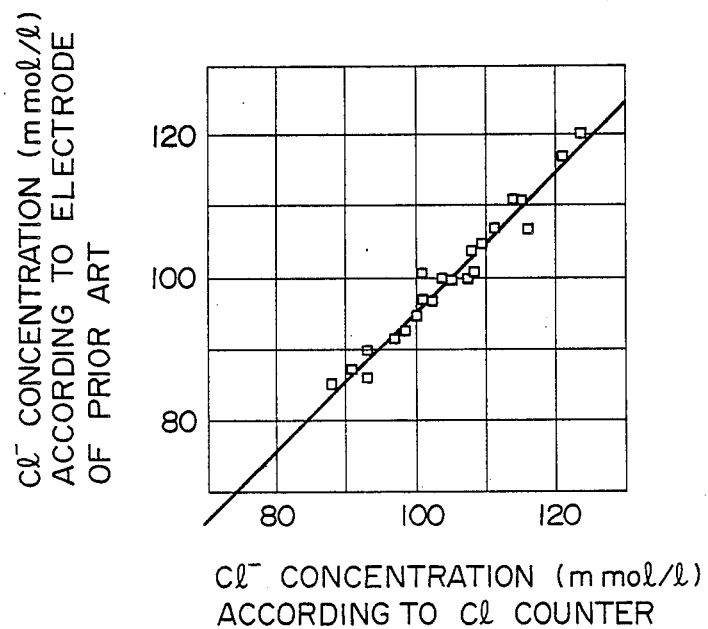

For comparison, FIG. 4 shows a correlation between measurements of chloride ion concentration of 22 species of commercially available, controlled serum by the electrode of the second example of the prior art and those by the coulometry method as the standard method. It is seen from FIG. 3 and FIG. 4 that a better correlation can be obtained with a smaller error of measurement according to the present invention (FIG. 3).

Figure 5:
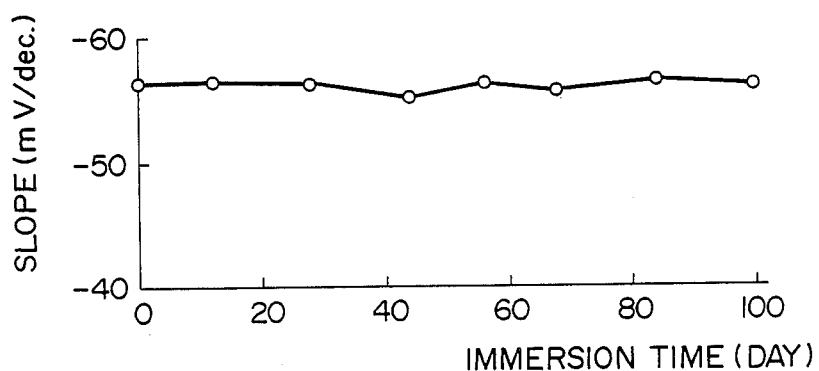
FIG. 5 is a diagram showing changes with the lapse of time in slope sensitivity of a chloride ion-selective electrode according to the present invention.

FIG. 5 shows changes in scope sensitivity when samples of commercially available, controlled serum were investigated with the electrode of the first preferred embodiment according to the present invention. It is obvious from FIG. 5 that the change in slope sensitivity is very small and thus the electrode according to the present invention has a long life with a high stability.

As mentioned above, the chloride ion-selective electrodes according to the present invention are far better than the prior art electrodes in that the electrodes according to the invention have a high selectivity over hydrophilic anions and lipophilic anions, and also have a good correlation to the standard method. Furthermore, the electrodes according to the present invention have a long effective life with a high stability. Thus, the present invention provides a novel chloride ion-selective electrode having a high utility in practice.

According to the present invention, a selectivity can be improved and a long time stability can be obtained by employing a tetraalkylammonium salt with four alkyl groups each having 10-24 carbon atoms as the chloride ion-sensitive substance, and a mixture of a linear alcohol with a low dielectric constant and an organic compound with a high dielectric constant as the plasticizer in a chloride ion-selective electrode, and thus measurement results with small errors can be effectively obtained, together with an advantage that the electrode of the present invention has a long life.

What we claim is:

1. A liquid film type, highly selective chloride ion-selective electrode with a long life, comprising: a sensitive film containing a polymeric material as a support film material, a tetraalkylammonium salt with four alkyl groups each having 10-24 carbon atoms as a chloride ion-sensitive substance, and a mixture of a linear alcohol having at least 10 carbon atoms with a dielectric constant of at most 10 and an organic compound with a dielectric constant higher than that of said linear alcohol as a plasticizer.

2. A liquid film type, chloride ion-selective electrode according to claim 1, wherein the sensitive film contains 3-30% by weight of the sensitive substance, 10-40% by weight of the linear alcohol, 3-20% by weight of the organic compound and 25-60% by weight of the polymeric material.

3. A liquid film type, chloride ion-selective electrode according to claim 1, wherein the linear alcohol is a linear alcohol having 10-20 carbon atoms with a dielectric constant of at most 10.

4. A liquid film type, chloride ion-selective electrode according to claim 1, wherein the linear alcohol is n-tetradecyl alcohol.

5. A liquid film type, chloride ion-selective electrode according to claim 1, wherein n-tetradecyl alcohol and n-tridecyl alcohol are used as the linear alcohols.

6. A liquid film type, chloride ion-selective electrode according to claim 1, wherein the polymeric material is selected from the group consisting of polyvinyl chlorides, polycarbonates, silicone rubbers and epoxy resins.

7. A liquid film type, chloride ion-selective electrode according to claim 1, wherein the tetralkylammonium salt is tetracetylammonium chloride.

8. A liquid film type, chloride ion-selective electrode according to claim 1, wherein the organic compound is o-nitrophenyloctylether.

9. A liquid film type, chloride ion-selective electrode according to claim I, wherein the organic compound is nitrobenzene.

10. A liquid film type, chloride ion-selective according to claim 1, wherein the organic compound has a dielectric constant of at least 15.

11. A liquid film type, chloride ion-selective electrode according to claim 1, wherein the organic compound is acetophenone.

12. A liquid film type, highly selective chloride ion-selective electrode with a long life, comprising: a sensitive film containing a polymeric material as a support film material, a tetraalkylammonium salt wherein the tetraalkylammonium salt is selected from the group consisting of tetradodecylammonium chloride, tetratetradecylammonium chloride, tetracetylammonium chloride and tetraoctadecylammonium chloride with four alkyl groups as a chloride ion-sensitive substance, and a mixture of a linear alcohol having at least 10 carbon atoms with a dielectric constant of at most 10 and an organic compound with a dielectric constant higher than that of said linear alcohol as a plasticizer.

13. A liquid film type, highly selective chloride ion-selective electrode with a long life, comprising a sensitive film containing a polymeric material as a support film material, a tetraalkylammonium salt, wherein the tetraalkylammonium salt is tetracetylamnonium chloride or tetraoctadecylammonium chloride with four alkyl groups as a chloride ion-sensitive substance, and a mixture of a linear alcohol having at least 10 carbon atoms with a dielectric constant of at most 10 and an organic compound with a dielectric constant higher than that of said linear alcohol as a plasticizer.

* * * * *